(12) United States Patent
Saoji (10) Patent No.: US 9,199,079 B2
(45) Date of Patent: Dec. 1, 2015

(54) METHODS AND SYSTEMS FOR OPTIMIZING SPEECH AND MUSIC PERCEPTION BY A BILATERAL COCHLEAR IMPLANT PATIENT

(71) Applicant: ADVANCED BIONICS AG, Staefa (CH)

(72) Inventor: Aniket Saoji, Ann Arbor, MI (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/359,287

(22) PCT Filed: Nov. 20, 2012

(86) PCT No.: PCT/US2012/066086
§ 371 (c)(1),
(2) Date: May 19, 2014

(87) PCT Pub. No.: WO2013/078218
PCT Pub. Date: May 30, 2013

(65) Prior Publication Data
US 2014/0277276 A1   Sep. 18, 2014

Related U.S. Application Data

(60) Provisional application No. 61/562,068, filed on Nov. 21, 2011.

(51) Int. Cl.
*A61N 1/36* (2006.01)

(52) U.S. Cl.
CPC .................................. *A61N 1/36032* (2013.01)

(58) Field of Classification Search
None
See application file for complete search history.

(56) References Cited

U.S. PATENT DOCUMENTS

| 8,027,734 B1 | 9/2011 | Saoji et al. | |
| 2008/0119910 A1* | 5/2008 | Daly et al. | 607/57 |
| 2009/0288489 A1* | 11/2009 | Lee et al. | 73/585 |

(Continued)

FOREIGN PATENT DOCUMENTS

| WO | WO-2007/090243 | 8/2007 |
| WO | WO-2010/115227 | 10/2010 |

(Continued)

OTHER PUBLICATIONS

Litvak, et al., Relationship between perception of spectral ripple and speech recognition in cochlear implant and vocoder listeners. J Acoust Soc Am. Aug. 2007;122(2):982-91.*

(Continued)

*Primary Examiner* — Brian T Gedeon
*Assistant Examiner* — Ankit Tejani
(74) *Attorney, Agent, or Firm* — ALG Intellectual Property, LLC (57) ABSTRACT

An exemplary method of optimizing speech and music perception by a bilateral cochlear implant patient includes identifying a first ear of a bilateral cochlear implant patient as being relatively more suited for processing speech than a second ear of the patient, directing a first cochlear implant subsystem associated with the first ear to operate in accordance with a first sound processing program configured to enhance speech perception by the patient, and directing a second cochlear implant subsystem associated with the second ear to operate in accordance with a second sound processing program configured to enhance music perception by the patient. Corresponding methods and systems are also disclosed.

18 Claims, 10 Drawing Sheets

(56) References Cited

U.S. PATENT DOCUMENTS

2010/0161000 A1* 6/2010 Litvak et al. ............. 607/57
2011/0077710 A1* 3/2011 Saoji et al. ............... 607/57
2011/0280427 A1 11/2011 Buyens

FOREIGN PATENT DOCUMENTS

| WO | WO 2010115227 A1 * | 10/2010 |
| WO | WO-2011/041156 | 4/2011 |
| WO | WO-2012/016009 | 2/2012 |
| WO | WO-2012/016011 | 2/2012 |

OTHER PUBLICATIONS

International Search Report and Written Opinion received in International Application No. PCT/US12/066086, dated Mar. 4, 2013.
Kallel, Fathi et al., "Dual-channel spectral subtraction algorithms based speech enhancement dedicated to a bilateral cochlear implant", *Applied Acoustics*, vol. 73, No. 1, Elsevier Ltd., (Jun. 23, 2011), pp. 12-20.
Garadat, Soha N., et al., "Effects of simulated spectral holes on speech intelligibility and spatial release from masking under binaural and monaural listening", *The Journal of the Acoustical Society of America*, vol. 127, No. 2, American Institute of Physics for the Acoustical Society of America, (Feb. 2010), pp. 977-989.
Tyler, Richard S., et al., "An Attempt to Improve Bilateral Cochlear Implants by Increasing the Distance between Electrodes and Providing Complementary Information to the Two Ears", *J Am Acad Audiol*, vol. 21, No. 1, (Jan. 2010), pp. 52-65.
Kokkinakis, Kostas et al., "Multi-microphone adaptive noise reduction strategies for coordinated stimulation in bilateral cochlear implant devices", *The Journal of the Acoustical Society of America*, vol. 127, No. 5, American Institute of Physics for the Acoustical Society of America, (May 2010), pp. 3136-3144.
Das, Subinoy et al., "Bilateral cochlear implantation: current concepts", *Current Opinion in Otolaryngology & Head and Neck Surgery*, vol. 13, No. 5, (Oct. 2005), pp. 290-293.

* cited by examiner

Fig. 10

METHODS AND SYSTEMS FOR OPTIMIZING SPEECH AND MUSIC PERCEPTION BY A BILATERAL COCHLEAR IMPLANT PATIENT

RELATED APPLICATIONS

The present application claims priority to U.S. Provisional Patent Application No. 61/562,068 by Aniket Saoji, filed on Nov. 21, 2011, and entitled "METHODS AND SYSTEMS FOR OPTIMIZING SPEECH AND MUSIC PERCEPTION BY A BILATERAL COCHLEAR IMPLANT PATIENT," the contents of which are hereby incorporated by reference in their entirety.

BACKGROUND INFORMATION

Bilateral cochlear implant prosthesis systems (i.e., cochlear implant systems that provide electrical stimulation to both ears of a patient) offer many advantages in terms of performance over conventional cochlear implant systems that are capable of only providing electrical stimulation to one of the patient's ears. For example, by applying electrical stimulation to both ears of a patient instead of one, bilateral cochlear implant systems are capable of providing a more realistic representation of audio content to the patient.

Unfortunately, however, some types of audio content are difficult for even bilateral cochlear implant patients to perceive. For example, bilateral cochlear implant patients often have a hard time accurately perceiving speech (e.g., lyrics) included in songs and other musical content, especially in the presence of ambient noise.

Unfortunately, traditional sound processing strategies that improve speech perception by a bilateral cochlear implant patient may diminish the quality of music as perceived by the patient. Likewise, traditional sound processing strategies that improve music perception by a bilateral cochlear implant patient (i.e., improve the quality of music as perceived by the patient) may diminish the ability of the patient to accurately perceive speech.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Exemplary methods and systems for optimizing speech and music perception by a bilateral cochlear implant patient are described herein. As will be described below, a sound processing optimization system may identify a first ear of a bilateral cochlear implant patient as being relatively more suited for processing speech than a second ear of the patient, direct a first cochlear implant subsystem associated with the first ear to operate in accordance with a first sound processing program configured to enhance speech perception by the patient, and direct a second cochlear implant subsystem associated with the second ear to operate in accordance with a second sound processing program configured to enhance music perception by the patient.

By using different sound processing programs for each ear of a bilateral cochlear implant patient, the methods and systems described herein may allow the bilateral cochlear implant patient to more accurately perceive speech and music compared to conventional sound processing techniques that use the same sound processing program for each ear. For example, most bilateral cochlear implant patients have one ear that is "better" at perceiving speech than the other ear (i.e., one ear that is more capable of encoding temporal and spectral modulations associated with speech than the other ear). Hence, by identifying the better ear and using a sound processing program configured to enhance speech perception for that ear, speech perception by the bilateral cochlear implant patient may be optimized. At the same time, by using a sound processing program configured to enhance music perception for the other ear, music perception by the bilateral cochlear implant patient may also be optimized. This is because the brain has the capability of combining separate information from both ears into a single percept.

Figure 1:
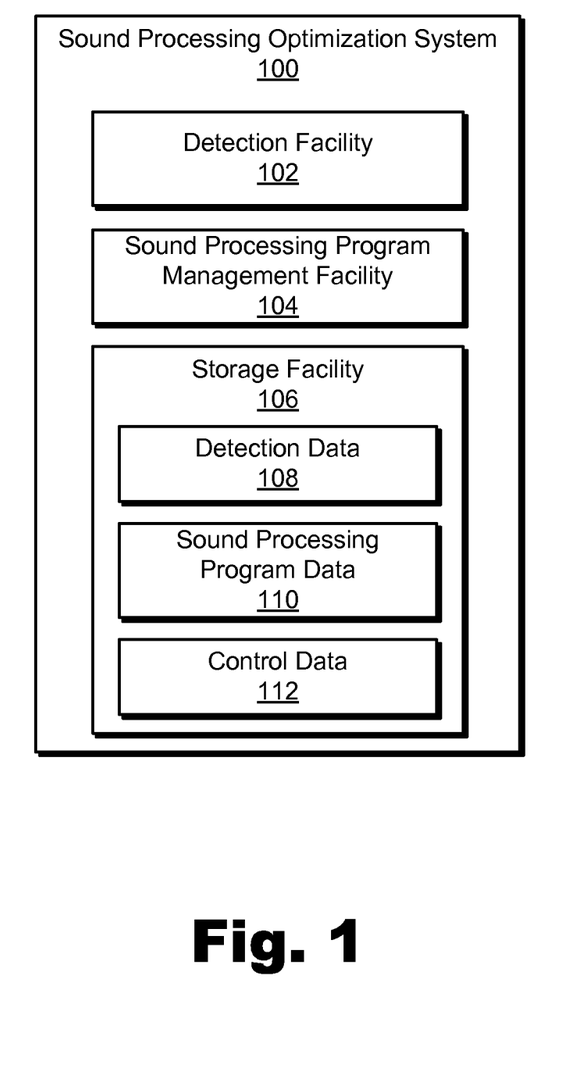
FIG. 1 illustrates an exemplary sound processing optimization system according to principles described herein.

FIG. 1 illustrates an exemplary sound processing optimization system 100 ("system 100"). As shown, system 100 may include, without limitation, a detection facility 102, a sound processing program management facility 104 ("program management facility 104"), and a storage facility 106 communicatively coupled to one another. It will be recognized that although facilities 102-106 are shown to be separate facilities in FIG. 1, any of facilities 102-106 may be combined into fewer facilities, such as into a single facility, or divided into more facilities as may serve a particular implementation.

Detection facility 102 may be configured to determine which ear of a bilateral cochlear implant patient is relatively more suited for processing speech. For example, detection facility 102 may identify a first ear of the bilateral cochlear implant patient as being relatively more suited for processing speech than a second ear of the patient. This may be performed in any suitable manner.

For example, detection facility 102 may determine that one of the patient's ears has a relatively better spectral resolution than the patient's other ear and designate the better ear as being more suited for processing speech. As used herein, "spectral resolution" associated with an ear of a patient refers to an ability of the patient to distinguish between a spectrally modulated stimulus (e.g., a stimulus that has a series of peaks and valleys) presented to the ear and a spectrally flat stimulus (e.g., a stimulus that does not have peaks and valleys) to the ear.

Figure 2A:
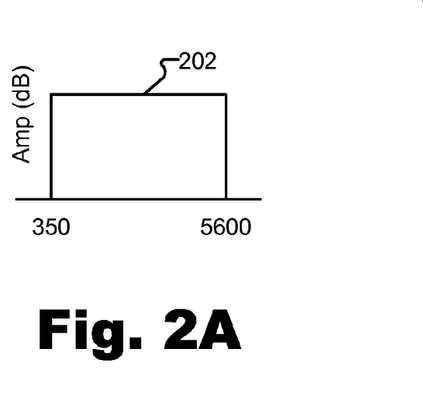
FIG. 2A shows an exemplary spectrally flat stimulus.
Figure 2B:
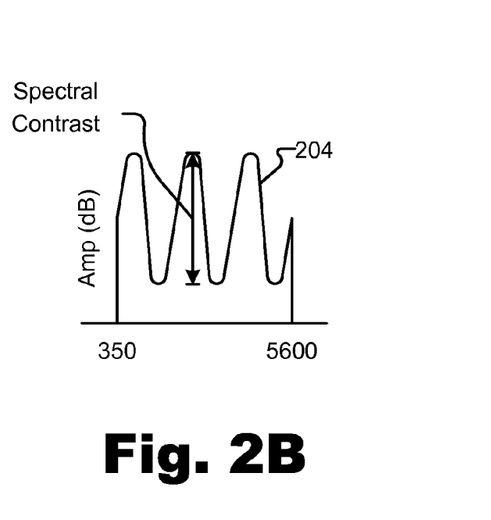
FIG. 2B shows an exemplary spectrally modulated stimulus.

To illustrate, FIG. 2A shows an exemplary spectrally flat stimulus 202 and FIG. 2B shows an exemplary spectrally modulated stimulus 204. As shown, spectrally flat stimulus 202 has a constant amplitude across the entire frequency range of interest. In contrast, spectrally modulated stimulus 204 includes a modulated waveform (e.g., a sinusoid) within the frequency range of interest. As shown in FIG. 2B, the peak-to-valley amplitude of the modulated waveform is referred to as the "spectral contrast" of spectrally modulated stimulus 204.

Hence, a relatively good spectral resolution indicates that the ear is capable of distinguishing between a spectrally modulated stimulus (e.g., spectrally modulated stimulus 204) that has a relatively small spectral contrast (i.e., a relatively small peak-to-valley amplitude) and a spectrally flat stimulus (e.g., spectrally flat stimulus 202). A relatively poor spectral resolution indicates that the ear is only capable of distinguishing between a spectrally modulated stimulus that has a relatively large spectral contrast (i.e., a relatively large peak-to-valley amplitude) and a spectrally flat stimulus.

In some examples, detection facility 102 may measure a spectral resolution of an ear by performing a spectral ripple test with respect to the ear. During an exemplary spectral ripple test, a spectral ripple test score is generated for the ear that indicates the smallest spectral contrast of a spectrally modulated stimulus that the ear is capable of detecting. Hence, an ear that has a relatively higher spectral ripple test score than another ear may be relatively more suited for processing speech than the other ear. Exemplary spectral ripple tests that may be used in accordance with the methods and systems described herein are described more fully in U.S. Pat. No. 8,027,734, which patent is incorporated herein by reference in its entirety.

In some alternative examples, detection facility 102 may identify a particular ear of a bilateral cochlear implant patient as being relatively more suited for processing speech in response to input provided by the patient. For example, during a fitting session in which a clinician fits bilateral cochlear implant system to a patient, the clinician may ask the patient which ear is better at processing speech. If the patient indicates a particular ear is better at perceiving speech, the clinician may direct detection facility 102 to designate the indicated ear as being relatively more suited for processing speech than the other ear of the patient.

In some examples, detection facility 102 may identify a particular ear of a bilateral cochlear implant patient as being relatively more suited for processing speech by detecting and processing one or more environmental factors associated with the patient. For example, detection facility 102 may initially identify the first ear of the patient as being relatively more suited for processing speech than the second ear. Subsequently, detection facility 102 may detect a change in one or more environmental factors that make the second ear relatively more suited for processing speech than the first ear. In response, as will be described below, the sound processing programs being applied to each ear may be modified and/or switched.

Exemplary environmental factors that may affect a capability of an ear to process speech include, but are not limited to, environmental noise, a location of the patient, and a location of a source of an audio signal being presented to the patient. For example, detection facility 102 may detect that an audio signal being presented to a patient includes speech content. Detection facility 102 may then determine that the audio signal is coming from a source relatively closer to the first ear than to the second ear of the patient. In response, detection facility 102 may designate the first ear as being relatively more suited for processing speech than the second ear. Subsequently, detection facility 102 may detect a change in relative position of the source with respect to the patient. For example, the patient may move with respect to the source of the audio signal in a manner that results in the source of the audio signal being relatively closer to the second ear than to the first ear. In response, detection facility 102 may designate the second ear as being relatively more suited for processing speech than the first ear.

With reference again to FIG. 1, program management facility 104 may be configured to perform one or more sound processing management operations. For example, in response to an identification of a first ear of a bilateral cochlear implant patient as being relatively more suited for processing speech than a second ear of the patient, program management facility 104 may direct a first cochlear implant subsystem associated with the first ear to operate in accordance with a first sound processing program configured to enhance speech perception by the patient. Program management facility 104 may be further configured to direct a second cochlear implant subsystem associated with the second ear to operate in accordance with a second sound processing program configured to enhance music perception by the patient.

The first sound processing program that may be used by the first cochlear implant subsystem associated with the first ear of the bilateral cochlear implant patient may include any suitable sound processing program configured to enhance speech perception by the patient. For example, the first sound processing program may include a "noise reduction" sound processing program configured to reduce an effect of ambient noise within the first cochlear implant subsystem.

Figure 3:
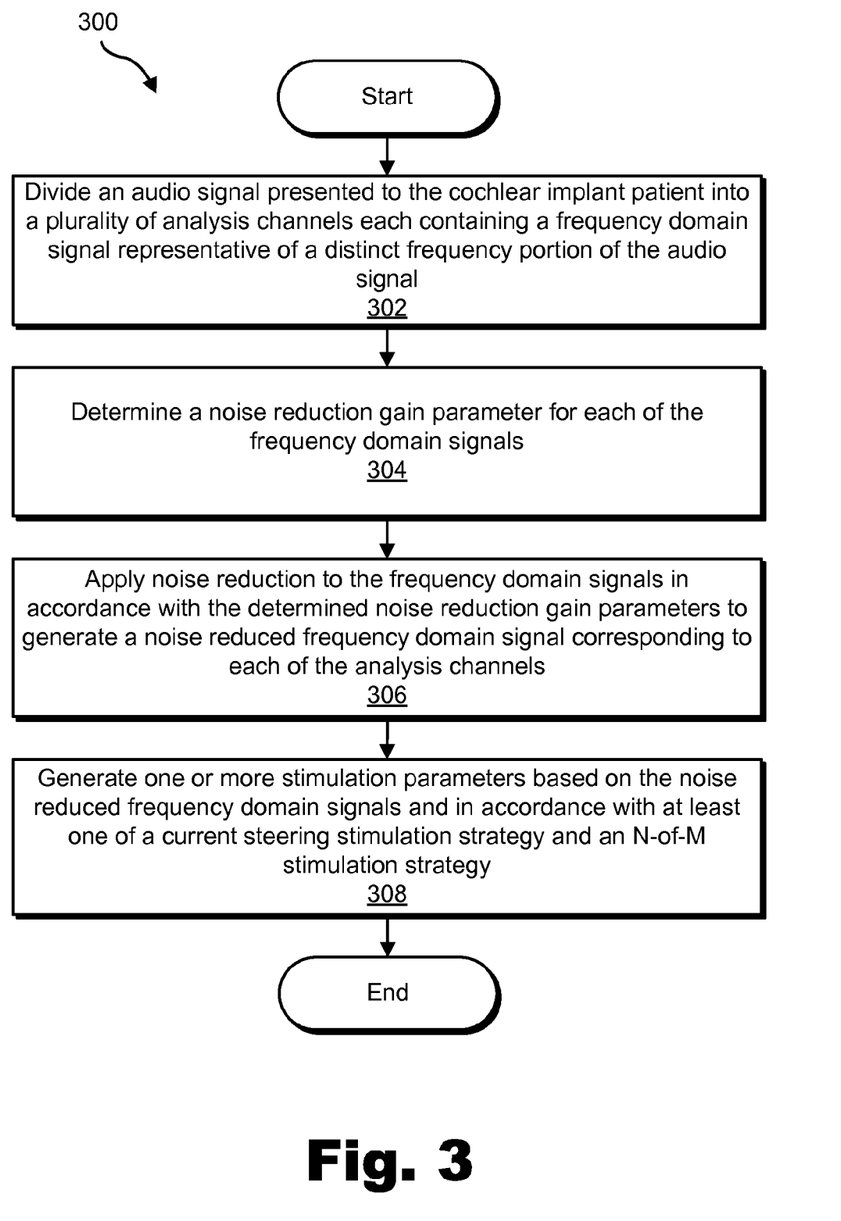
FIG. 3 illustrates an exemplary method of reducing an effect of ambient noise that may be performed by a cochlear implant subsystem in accordance with a noise reduction sound processing program according to principles described herein.

FIG. 3 illustrates an exemplary method 300 of reducing an effect of ambient noise that may be performed by a cochlear implant subsystem in accordance with a noise reduction sound processing program configured to enhance speech perception by a bilateral cochlear implant patient. While FIG. 3 illustrates exemplary steps according to one embodiment, other embodiments may omit, add to, reorder, and/or modify any of the steps shown in FIG. 3. Method 300, as well as other embodiments related to noise reduction sound processing programs that may be employed by the methods and systems described herein, is more fully described in co-pending U.S. patent application Ser. No. 12/879,603, entitled "Methods and Systems for Reducing an Effect of Ambient Noise Within an Auditory Prosthesis System," filed Sep. 10, 2010, and incorporated herein by reference in its entirety.

In step 302, an audio signal presented to a bilateral cochlear implant patient is divided into a plurality of analysis channels each containing a frequency domain signal representative of a distinct frequency portion of the audio signal.

In step 304, a noise reduction gain parameter is determined for each of the frequency domain signals provided in step 302. The noise reduction gain parameter for each of the frequency domain signals may be determined in any suitable manner. For example, the noise reduction gain parameter for each of the frequency domain signals may be based on a signal-to-noise ratio of each of the frequency domain signals.

In step 306, noise reduction is applied to the frequency domain signals in accordance with the noise reduction gain parameters determined in step 304 to generate a noise reduced frequency domain signal corresponding to each of the analysis channels.

In step 308, one or more stimulation parameters based on the noise reduced frequency domain signals are generated in accordance with at least one of a current steering stimulation strategy and an N-of-M stimulation strategy. Exemplary implementations of a current steering stimulation strategy and an N-of-M stimulation strategy are described in the above-referenced co-pending U.S. patent application Ser. No. 12/879,603.

Likewise, the second sound processing program that may be used by the second cochlear implant subsystem associated with the second ear of the bilateral cochlear implant patient may include any suitable sound processing program configured to enhance music perception by the patient. For example, the second sound processing program may include a "phantom electrode stimulation" sound processing program. "Phantom electrode stimulation" refers to a stimulation strategy that may be used to expand a range of pitches or frequencies that may be presented to a cochlear implant patient (and thereby improve music perception by the patient). In phantom electrode stimulation, compensation current is applied to one or more compensating electrodes in order to produce sound having a pitch that is lower than a pitch associated with a particular electrode (e.g., the most apical electrode) or a sound having a pitch that is higher than a pitch associated with a particular electrode (e.g., the most basal electrode).

Figure 4:
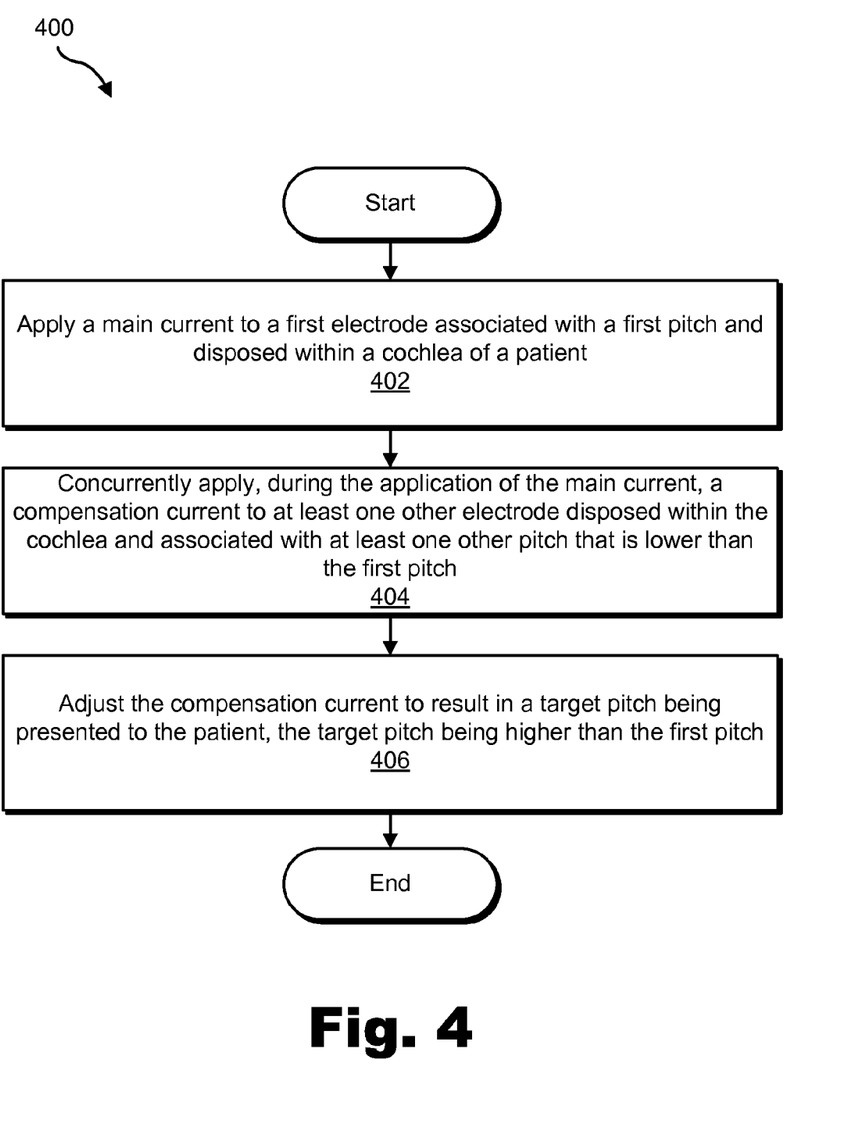
FIG. 4 illustrates an exemplary phantom electrode stimulation method that may be performed by a cochlear implant subsystem in accordance with a phantom electrode stimulation sound processing program according to principles described herein.

For example, FIG. 4 illustrates an exemplary phantom electrode stimulation method 400 that may be performed by a cochlear implant subsystem in accordance with a phantom electrode stimulation sound processing program configured to enhance music perception by a bilateral cochlear implant patient. While FIG. 4 illustrates exemplary steps according to one embodiment, other embodiments may omit, add to, reorder, and/or modify any of the steps shown in FIG. 4. Method 400, as well as other embodiments related to phantom electrode stimulation, is more fully described in co-pending U.S. patent application Ser. No. 12/644,350, entitled "Compensation Current Optimization for Cochlear Implant Systems," filed Dec. 22, 2010, and incorporated herein by reference in its entirety.

In step 402, a main current is applied to a first electrode associated with a first pitch and disposed within a cochlea of a patient. The first electrode may include a most basal electrode included in an array of electrodes disposed in the cochlea or any other electrode included in the electrode array.

In step 404, a compensation current is concurrently applied during the application of the main current to at least one other electrode disposed within the cochlea and associated with at least one other pitch that is lower than the first pitch. The at least one other electrode may include any number of electrodes in the array of electrodes as may serve a particular implementation.

In step 406, the compensation current is adjusted to result in a target pitch being presented to the patient, the target pitch being higher than the first pitch. The compensation current may be adjusted in any of the ways described in the above-referenced co-pending U.S. patent application Ser. No. 12/644,350.

Figure 5:
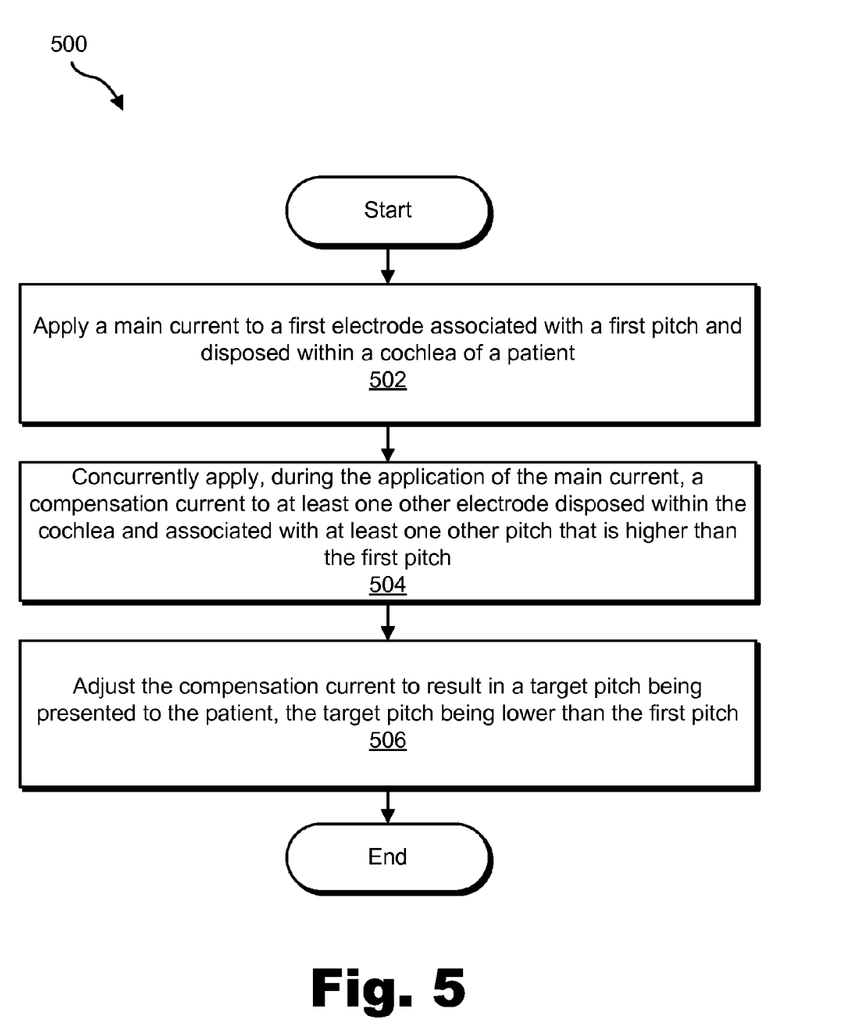
FIG. 5 illustrates another exemplary phantom electrode stimulation method that may be performed by a cochlear implant subsystem in accordance with a phantom electrode stimulation sound processing program according to principles described herein.

FIG. 5 illustrates another phantom electrode stimulation method 500 that may be performed by a cochlear implant subsystem in accordance with a phantom electrode stimulation sound processing program configured to enhance music perception by a bilateral cochlear implant patient. While FIG. 5 illustrates exemplary steps according to one embodiment, other embodiments may omit, add to, reorder, and/or modify any of the steps shown in FIG. 5. Method 500 is more fully described in the above-referenced co-pending U.S. patent application Ser. No. 12/644,350.

In step 502, a main current is applied to a first electrode associated with a first pitch and disposed within a cochlea of a patient. The first electrode may include a most apical electrode included in an array of electrodes disposed in the cochlea or any other electrode included in the electrode array.

In step 504, a compensation current is concurrently applied during the application of the main current to at least one other electrode disposed within the cochlea and associated with at least one other pitch that is higher than the first pitch. The at least one other electrode may include any number of electrodes in the array of electrodes as may serve a particular implementation.

In step 506, the compensation current is adjusted to result in a target pitch being presented to the patient, the target pitch being lower than the first pitch. The compensation current may be adjusted in any of the ways described in the above-referenced co-pending U.S. patent application Ser. No. 12/644,350.

It will be recognized that the exemplary sound processing programs described in connection with FIGS. 3-5 are merely illustrative of the many different sound processing programs that may be used to enhance speech and/or music perception by a bilateral cochlear implant patient.

Returning to FIG. 1, program management facility 104 may be configured to direct a cochlear implant subsystem to operate in accordance with a particular sound processing program in any suitable manner. For example, program management facility 104 may transmit control data representative of one or more control parameters to the cochlear implant subsystem. The one or more control parameters may be configured to govern an operation of the cochlear implant subsystem by directing the cochlear implant system to operate in accordance with a particular sound processing program.

In some examples, program management facility 104 may be further configured to detect an audio signal that includes both speech content and music content, separate the audio signal into a first signal comprising the speech content and a second signal comprising the music content, and provide the first cochlear implant subsystem with the first signal and the second cochlear implant subsystem with the second signal. By so doing, each cochlear implant subsystem may more effectively provide electrical stimulation representative of the speech content and the music content. The audio signal may be separated using any suitable filter heuristic as may serve a particular implementation.

Storage facility 106 may be configured to maintain detection data 108 generated and/or used by detection facility 102, sound processing program data 110 generated and/or used by program management facility 104, and/or control data 112 generated and/or used by program management facility 104. It will be recognized that storage facility 106 may maintain additional or alternative data as may serve a particular implementation.

Various implementations of system 100 will now be described. It will be recognized that the various implementations of system 100 described herein are merely illustrative of the many possible implementations of system 100.

Figure 6:
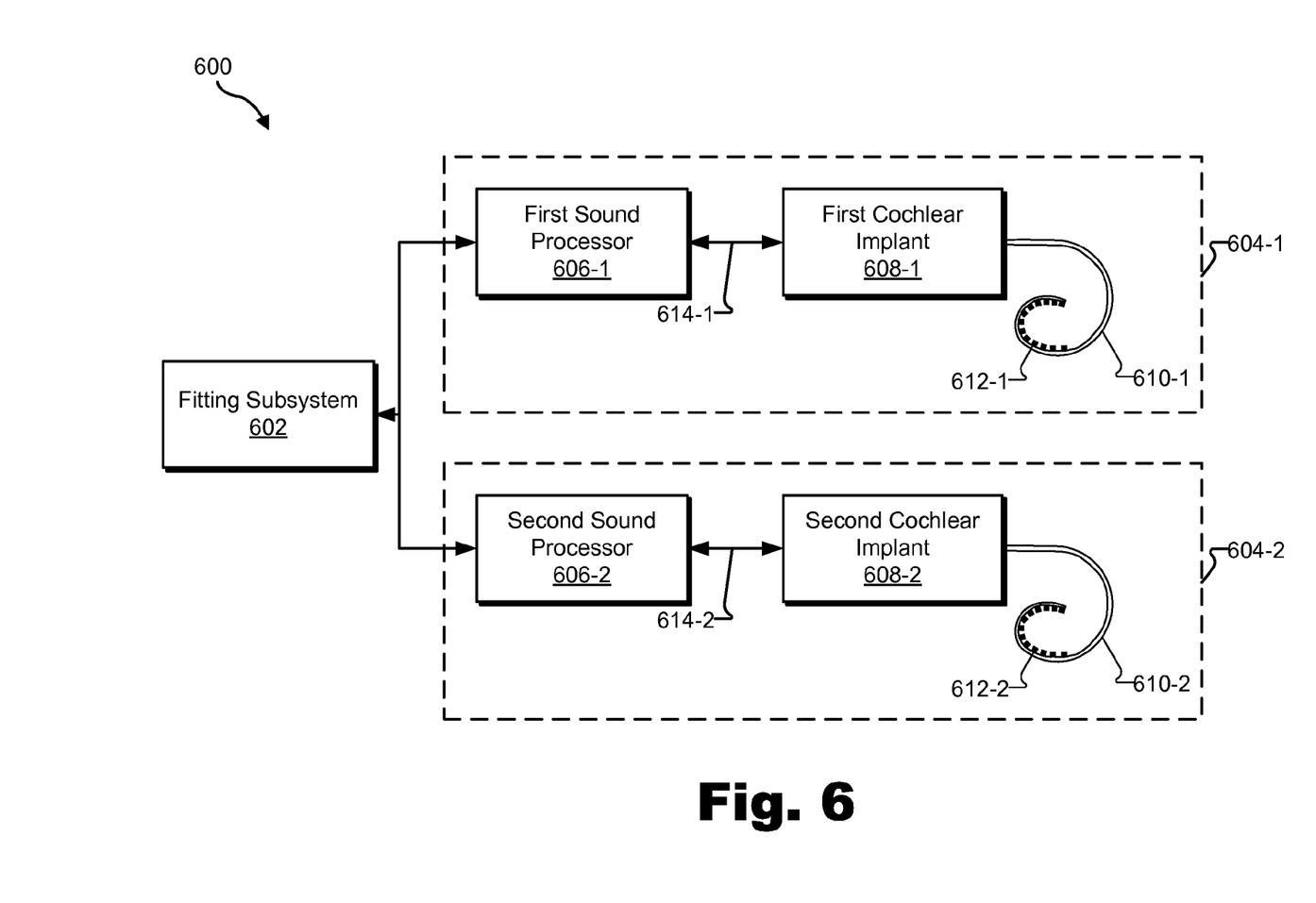
FIGS. 6-8 illustrate exemplary implementations of the system of FIG. 1 according to principles described herein.

FIG. 6 illustrates an exemplary implementation 600 of system 100 in which a fitting subsystem 602 is selectively and communicatively coupled to a first cochlear implant subsystem 604-1 and a second cochlear implant subsystem 604-2 (collectively "cochlear implant subsystems 604"). Fitting subsystem 602 and cochlear implant subsystems 604 may communicate using any suitable communication technologies, devices, networks, media, and protocols supportive of data communications.

Fitting subsystem 602 may be configured to perform one or more fitting operations with respect to cochlear implant subsystems 604. For example, fitting subsystem 602 may be used to load one or more sound processing programs cochlear implant subsystems 604, perform one or more tests (e.g., spectral ripple tests) with respect to the cochlear implant subsystems 604, and/or otherwise fit cochlear implant subsystems 604 to a bilateral cochlear implant patient. To this end, fitting subsystem 602 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

As shown, each cochlear implant subsystem 604 (also referred to as a cochlear implant system) may include a sound processor 606 (e.g., first sound processor 606-1 and second sound processor 606-2), a cochlear implant 608 (e.g., first cochlear implant 608-1 and second cochlear implant 608-2), and an electrode lead 610 (e.g., electrode lead 610-1 and electrode lead 610-2). Each electrode lead may have a plurality of electrodes (e.g., electrodes 612-1 and 612-2) disposed thereon.

Each sound processor 606 may include any suitable device configured to process audio signals presented to a bilateral cochlear implant patient and/or control an operation of cochlear implants 608. In some examples, each sound processor 606 is implemented by an externally worn unit (e.g., a behind-the-ear device, a body worn device, etc.). Alternatively, each sound processor 606 may be configured to be at least partially implanted within the patient.

In some examples, each sound processor 606-1 and 606-2 is configured to operate (e.g., concurrently) in accordance with a particular sound processing program. For example, first sound processor 606-1 may be configured to operate in accordance with a first sound processing program configured to enhance speech perception by the patient and second sound processor 606-2 may be configured to operate in accordance with a second sound processing program configured to enhance music perception by the patient. To illustrate, first sound processor 606-1 may direct first cochlear implant 608-1 to generate and apply electrical stimulation representative of speech content to one or more stimulation sites within the first ear of a patient in accordance with the first sound processing program. Likewise, second sound processor 606-2 may direct second cochlear implant 608-2 to generate and apply electrical stimulation representative of music content to one or more stimulation sites within the second ear of the patient in accordance with the second sound processing program.

Cochlear implants 608 may each include any suitable auditory prosthesis configured to be at least partially implanted within a patient as may serve a particular implementation. For example, each cochlear implant 608 may include an implantable cochlear stimulator, a brainstem implant and/or any other type of auditory prosthesis.

In some examples, cochlear implants 608 may be configured to be implanted on opposite sides of a patient's head in order to apply electrical stimulation representative of one or more audio signals by way of one or more of electrodes 612 to one or more stimulation sites associated with the auditory pathways (e.g., the auditory nerves) of the patient. For example, first cochlear implant 608-1 may be implanted on a right side of a patient's head in order to provide electrical stimulation to one or more stimulation sites within the patient's right cochlea. Likewise, second cochlear implant 608-2 may be implanted on a left side of the patient's head in order to provide electrical stimulation to one or more stimulation sites within the patient's left cochlea.

Sound processors 606 and cochlear implants 608 may communicate by way of communication channel 614. Communication channel 614 may be wired or wireless as may serve a particular implementation.

Figure 7:
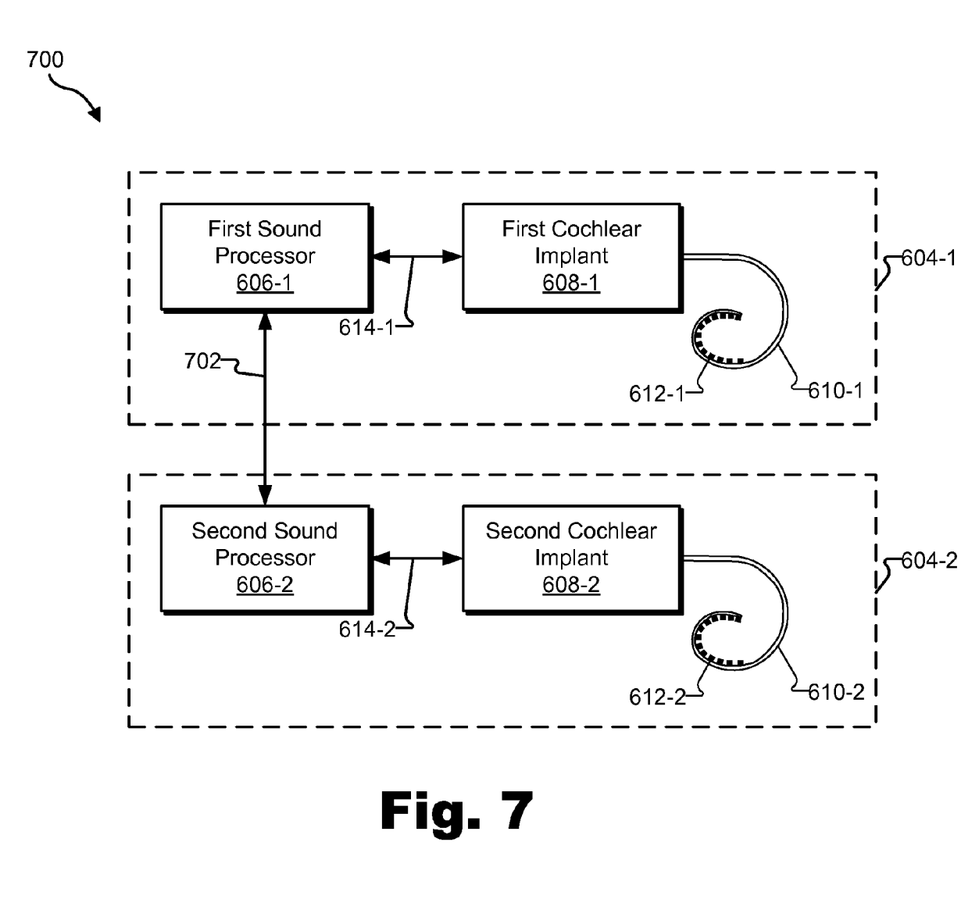

FIG. 7 illustrates an exemplary implementation 700 of system 100. Implementation 700 is similar to implementation 600, but does not include fitting subsystem 602. Instead, first and second sound processors 606-1 and 606-2 may be configured to communicate with each other by way of communication channel 702. For example, first sound processor 606-1 may detect a change in one or more environmental factors and communicate data representative of the change to second sound processor 606-2 by way of communication channel 702. In this manner, each sound processor 606 may switch to a different sound processing program in accordance with the detected change in the one or more environmental factors.

Figure 8:
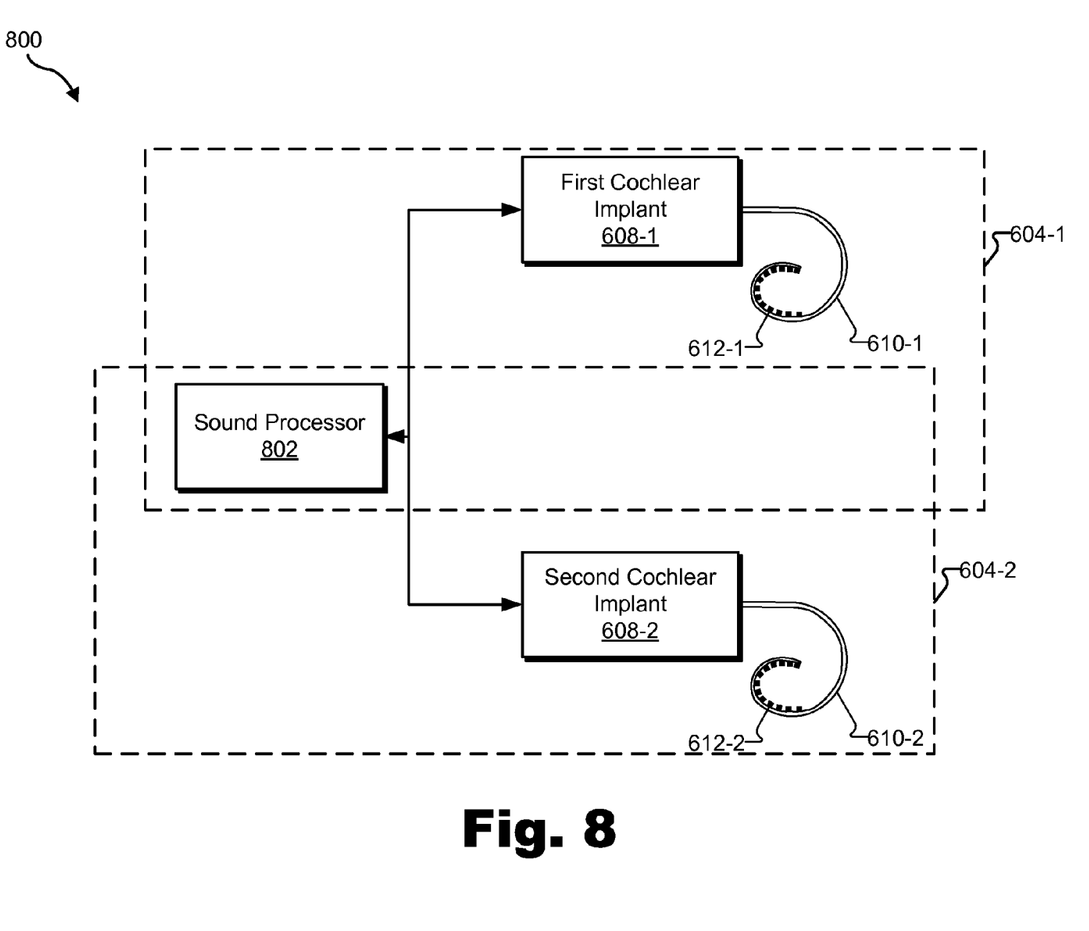

FIG. 8 illustrates an exemplary implementation 800 of system 100. In implementation 800, a single sound processor 802 is communicatively coupled to each cochlear implant 608. Hence, sound processor 802 is shown to be included in both cochlear implant subsystems 604-1 and 604-2. Sound processor 802 may communicate with cochlear implants 608 in any suitable manner.

In certain embodiments, the facilities of system 100 may be implemented by any combination of components illustrated in FIGS. 6-8. For example, the facilities of system 100 may be implemented entirely by fitting subsystem 602 or by first and/or second cochlear implant subsystems 604-1 and/or 604-2. In other embodiments, the facilities of system 100 may be distributed across any combination of fitting subsystem 602 and cochlear implant subsystems 604.

Figure 9:
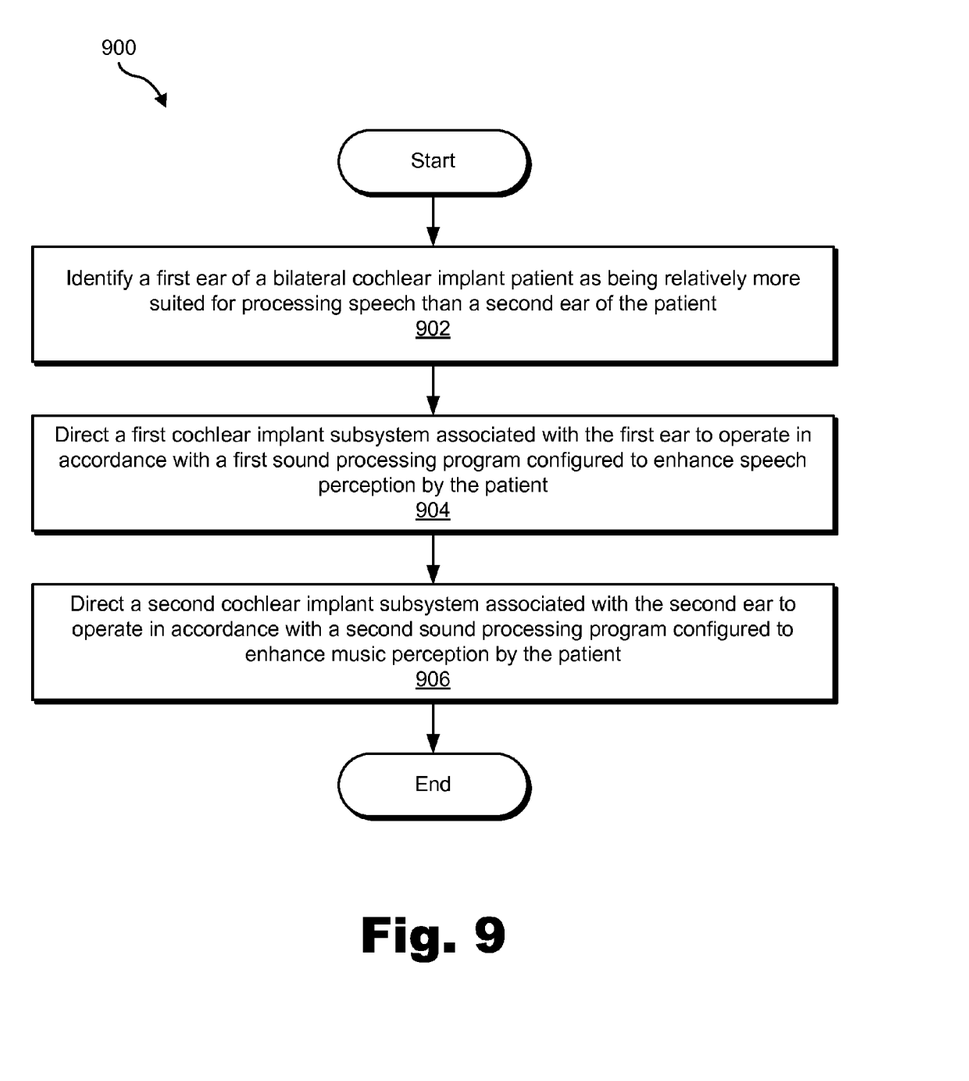
FIG. 9 illustrates an exemplary method of optimizing speech and music perception by a bilateral cochlear implant patient according to principles described herein.

FIG. 9 illustrates an exemplary method 900 of optimizing speech and music perception by a bilateral cochlear implant patient. While FIG. 9 illustrates exemplary steps according to one embodiment, other embodiments may omit, add to, reorder, and/or modify any of the steps shown in FIG. 9. One or more of the steps shown in FIG. 9 may be performed by system 100 and/or any implementation thereof.

In step 902, a sound processing optimization system identifies a first ear of a bilateral cochlear implant patient as being relatively more suited for processing speech than a second ear of the patient. Step 902 may be performed in any of the ways described herein.

In step 904, the sound processing optimization system directs a first cochlear implant subsystem associated with the first ear to operate in accordance with a first sound processing program configured to enhance speech perception by the patient. Step 904 may be performed in any of the ways described herein.

In step 906, the sound processing optimization system directs a second cochlear implant subsystem associated with the second ear to operate in accordance with a second sound processing program configured to enhance music perception by the patient. Step 906 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 10:
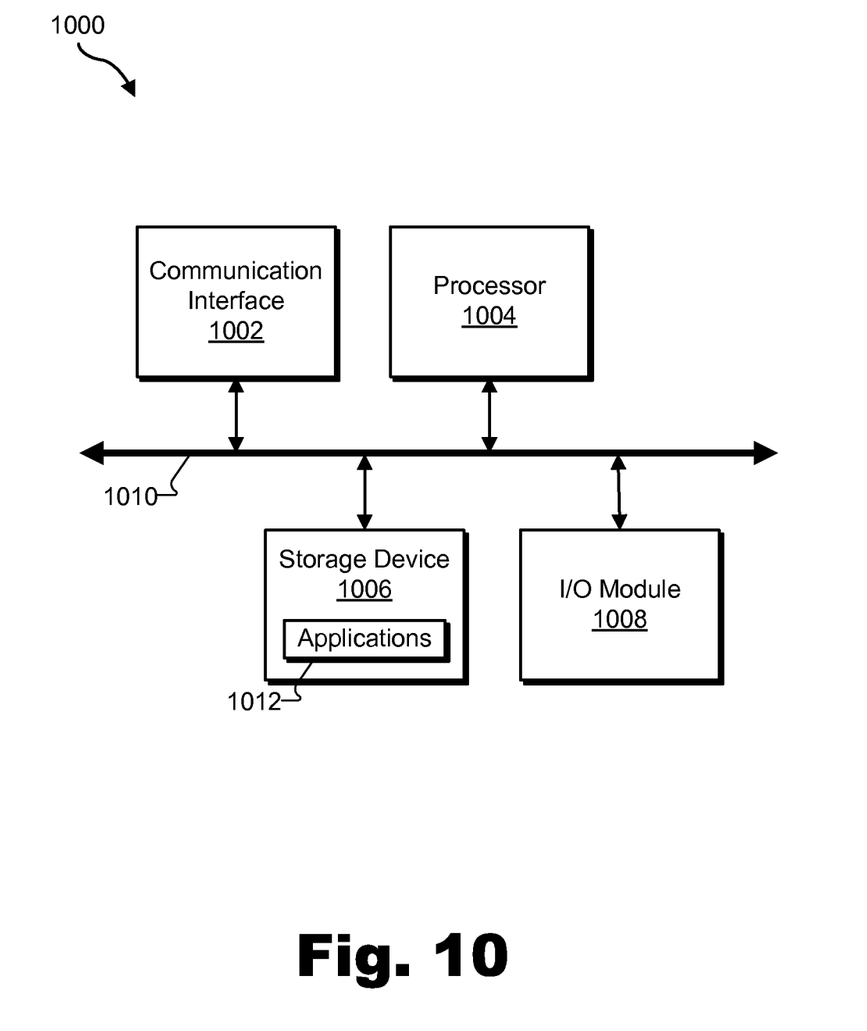
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with any of the facilities and/or subsystems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
identifying, by a sound processing optimization system, a first ear of a bilateral cochlear implant patient as being relatively more suited for processing speech than a second ear of the patient;
directing, by the sound processing optimization system, a first cochlear implant subsystem associated with the first ear to operate in accordance with a first sound processing program configured to enhance speech perception by the patient;
directing, by the sound processing optimization system, a second cochlear implant subsystem associated with the second ear to operate in accordance with a second sound processing program configured to enhance music perception by the patient;
detecting, by the sound processing optimization system subsequent to the identifying, a change in one or more environmental factors that make the second ear relatively more suited for processing speech than the first ear;
directing, by the sound processing optimization system in response to the detecting of the change in one or more environmental factors, the first cochlear implant subsystem to dynamically switch to operating in accordance with the second sound processing program configured to enhance music perception by the patient; and
directing, by the sound processing optimization system in response to the detecting of the change in one or more environmental factors, the second cochlear implant subsystem to dynamically switch to operating in accordance with the first sound processing program configured to enhance speech perception by the patient.

2. The method of claim 1, wherein the identifying of the first ear as being relatively more suited for processing speech than the second ear comprises determining that the first ear has a relatively better spectral resolution than the second ear.

3. The method of claim 2, wherein the determining that the first ear has the relatively better spectral resolution comprises determining that the first ear has a higher spectral ripple test score than the second ear.

4. The method of claim 1, wherein the identifying of the first ear as being relatively more suited for processing speech than the second ear comprises:
   detecting input provided by the patient that is representative of a selection of the first ear as being better at processing speech than the second ear; and
   designating, in response to the input, the first ear as being relatively more suited for processing speech than the second ear.

5. The method of claim 1, wherein the identifying of the first ear as being relatively more suited for processing speech than the second ear comprises:
   detecting that an audio signal being presented to the patient includes speech content;
   determining that the audio signal is coming from a source relatively closer to the first ear than to the second ear; and
   designating, in response to the determining, the first ear as being relatively more suited for processing speech than the second ear.

6. The method of claim 1, wherein the change in one or more environmental factors comprises a change in a position of a source of an audio signal comprising speech content relative to the patient.

7. The method of claim 1, further comprising:
   detecting, by the sound processing optimization system, an audio signal that includes both speech content and music content;
   separating, by the sound processing optimization system, the audio signal into a first signal comprising the speech content and a second signal comprising the music content; and
   providing, by the sound processing optimization system while the first cochlear implant subsystem operates in accordance with the first sound processing program and while the second cochlear implant subsystem operates in accordance with the second sound processing program, the first cochlear implant subsystem with the first signal and the second cochlear implant subsystem with the second signal.

8. The method of claim 1, wherein the first sound processing program configured to enhance speech perception by the patient comprises a noise reduction sound processing program.

9. The method of claim 1, wherein the second sound processing program configured to enhance music perception by the patient comprises a phantom electrode stimulation sound processing program.

10. The method of claim 1, embodied as computer-executable instructions on at least one non-transitory computer-readable medium.

11. A system comprising:
    a detection facility that identifies a first ear of a bilateral cochlear implant patient as being relatively more suited for processing speech than a second ear of the patient; and
    a sound processing program management facility communicatively coupled to the detection facility and that directs a first cochlear implant subsystem associated with the first ear to operate in accordance with a first sound processing program configured to enhance speech perception by the patient, and
    directs a second cochlear implant subsystem associated with the second ear to operate in accordance with a second sound processing program configured to enhance music perception by the patient,
    wherein:
    the detection facility detects, subsequent to the identifying, a change in one or more environmental factors that make the second ear relatively more suited for processing speech than the first ear; and
    the sound processing program management facility
       directs, in response to the detection of the change in one or more environmental factors, the first cochlear implant subsystem to dynamically switch to operating in accordance with the second sound processing program configured to enhance music perception by the patient, and
       directs, in response to the detection of the change in one or more environmental factors, the second cochlear implant subsystem to dynamically switch to operating in accordance with the first sound processing program configured to enhance speech perception by the patient.

12. The system of claim 11, wherein the detection facility identifies the first ear as being relatively more suited for processing speech than the second ear by determining that the first ear has a relatively better spectral resolution than the second ear.

13. The system of claim 11, wherein the detection facility identifies the first ear as being relatively more suited for processing speech than the second ear by:
    detecting input provided by the patient that is representative of a selection of the first ear as being better at processing speech than the second ear; and
    designating, in response to the input, the first ear as being relatively more suited for processing speech than the second ear.

14. The system of claim 11, wherein the detection facility identifies the first ear as being relatively more suited for processing speech than the second ear by:
    detecting that an audio signal being presented to the patient includes speech content;
    determining that the audio signal is coming from a source relatively closer to the first ear than to the second ear; and
    designating, in response to the determining, the first ear as being relatively more suited for processing speech than the second ear.

15. The system of claim 11, wherein the first sound processing program configured to enhance speech perception by the patient comprises a noise reduction sound processing program.

16. The system of claim 11, wherein the second sound processing program configured to enhance music perception by the patient comprises a phantom electrode stimulation sound processing program.

17. The system of claim 11, wherein the change in one or more environmental factors comprises a change in a position of a source of an audio signal comprising speech content relative to the patient.

18. The system of claim 11, wherein:
    the detection facility detects an audio signal that includes both speech content and music content; and
    the sound processing program management facility
       separates the audio signal into a first signal comprising the speech content and a second signal comprising the music content, and
       provides, while the first cochlear implant subsystem operates in accordance with the first sound processing program and while the second cochlear implant subsystem operates in accordance with the second sound processing program, the first cochlear implant subsystem with the first signal and the second cochlear implant subsystem with the second signal.

* * * * *